United States Patent [19]

Compton

[11] 4,010,554
[45] Mar. 8, 1977

[54] ANATOMICAL DISPLAY DEVICE AND PROCESS FOR PREPARING AND DISPLAYING ANATOMICAL ORGAN SPECIMENS

[76] Inventor: Robert W. Compton, 635 E. State Ave., Meridian, Idaho 83642

[22] Filed: Feb. 13, 1976

[21] Appl. No.: 657,843

[52] U.S. Cl. .................................... 35/20; 35/51
[51] Int. Cl.² ...................................... G09B 23/30
[58] Field of Search ............. 35/16, 17, 20, 51, 41; 352/39

[56] References Cited

UNITED STATES PATENTS

| 1,141,480 | 6/1915 | Murayama | 35/17 |
|---|---|---|---|
| 2,444,729 | 7/1948 | Crockwell | 352/39 |
| 2,776,596 | 1/1957 | Elgen | 35/20 X |
| 2,996,762 | 8/1961 | McCormick | 35/20 X |
| 3,137,080 | 6/1964 | Zang | 35/41 |
| 3,369,299 | 2/1968 | Thomas | 35/16 X |

Primary Examiner—Harland S. Skogquist
Attorney, Agent, or Firm—Wells, St. John & Roberts

[57] ABSTRACT

A process is described by which macroscopic anatomical organ specimens are sliced into sections of equal thickness and arranged in a serial array within a transparent container for visual display. The process includes the steps of (1) suspending the anatomical organ within a block of transparent agar solution; (2) slicing the suspended organ and surrounding agar into sections of equal thickness; (3) pouring a liquid preservative into an upwardly open transparent container; (4) arranging the sliced sections in a prescribed array within the container; (5) pressing a transparent cover plate over the sections in the container to remove air from between the plates; and (6) affixing the transparent cover plate to the container to hermetically seal the sections and liquid preservative within the container under the transparent plate. The device for displaying serialed macroscopic sections of a sliced anatomical organ includes two planar transparent opposed plates. One is used as a base plate and includes upright peripheral side walls. This plate and side walls comprise a container in which the array of sections are received. The other plate becomes a cover that is complementary to the area confined by the peripheral walls. To complete the display, the cover plate is positioned over sections held on the base plate. Once air has been removed from between the two plates, the cover plate is affixed to the side walls. The display is then hermetically sealed to preserve the contents between the two plates for an indefinite period of time.

15 Claims, 9 Drawing Figures

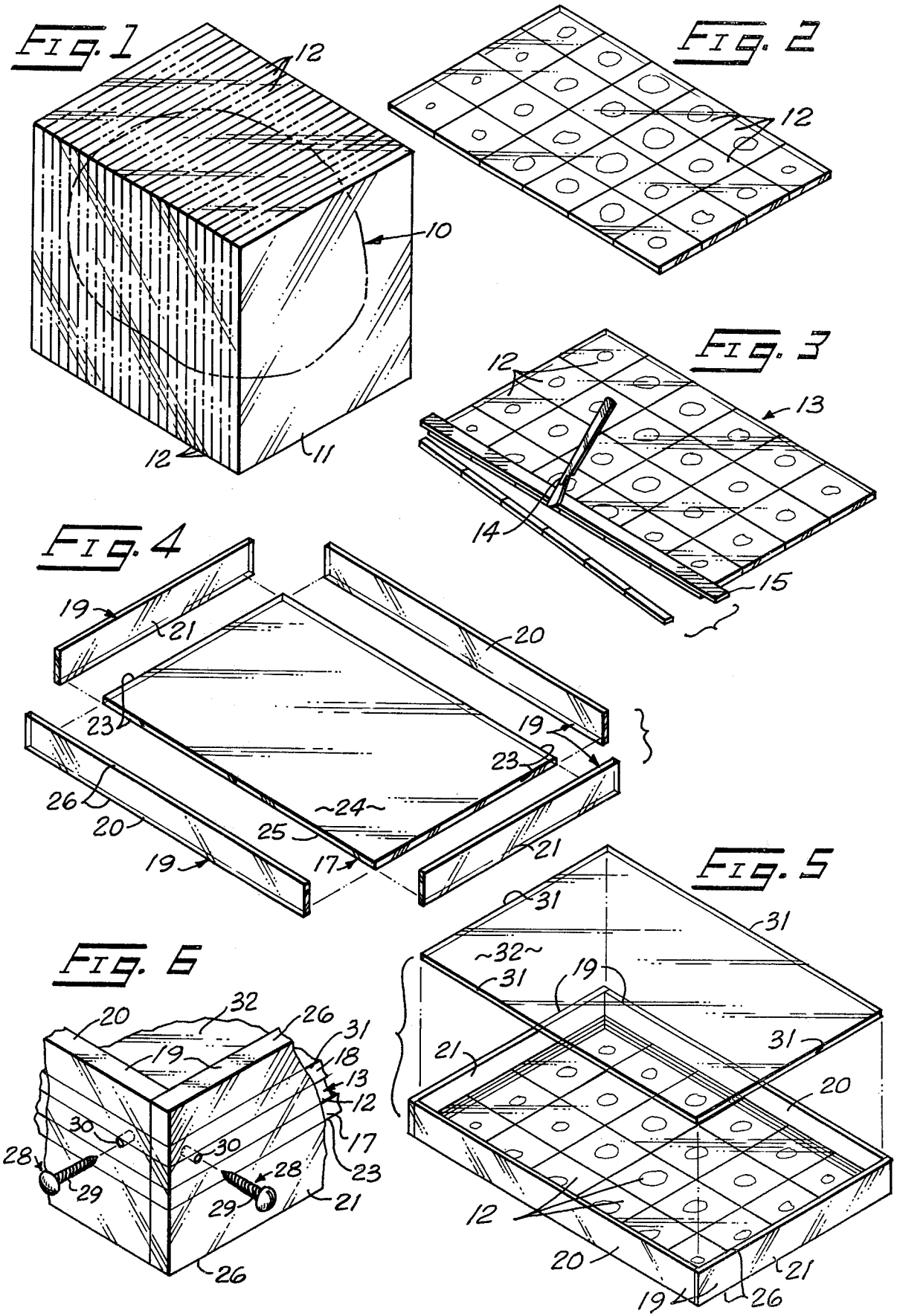

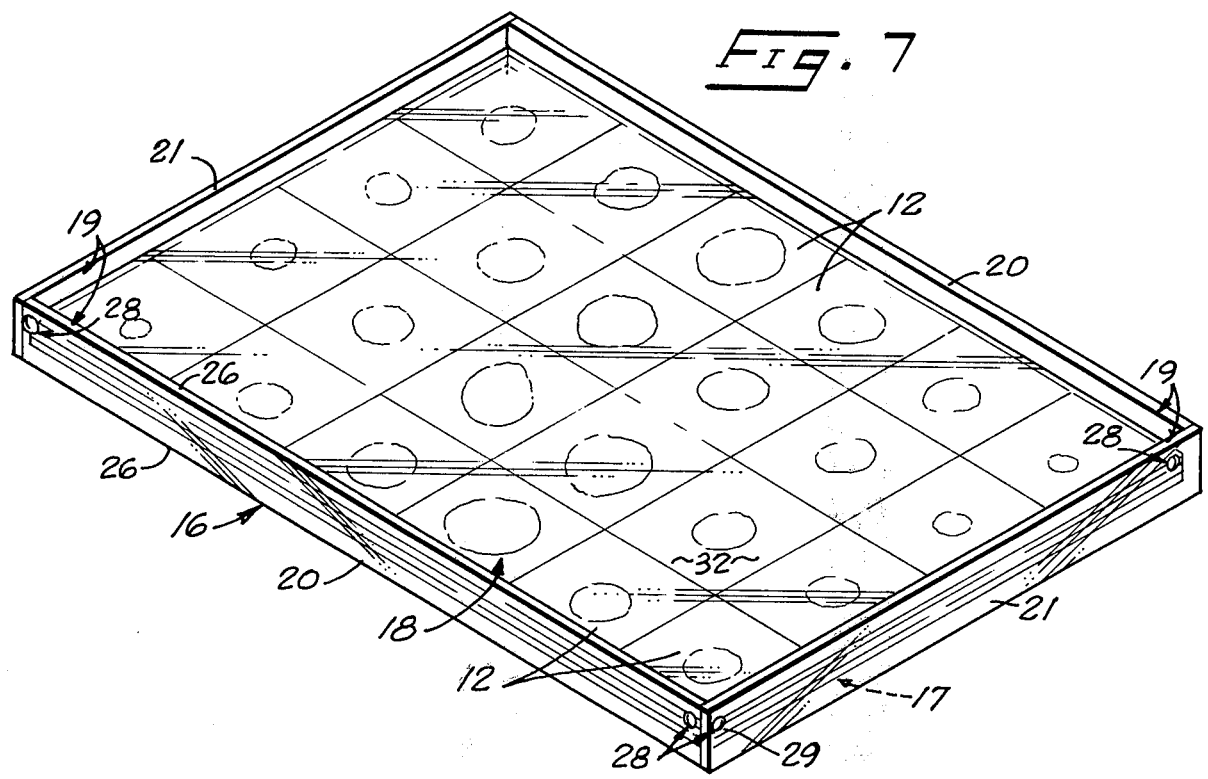
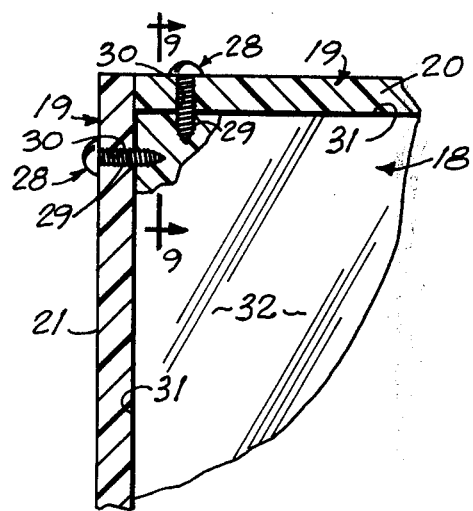
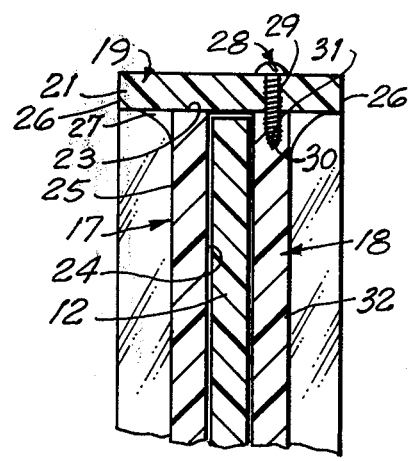

ANATOMICAL DISPLAY DEVICE AND PROCESS FOR PREPARING AND DISPLAYING ANATOMICAL ORGAN SPECIMENS

BACKGROUND OF THE INVENTION

The current trend in biological education is to incorporate more laboratory study of the nervous system in high school and college level curriculum. Thus there is a market for permanently displayed macroscopic anatomical organs, especially well-preserved dissected organs. However, the problem is that wet stored specimens deteriorate rapidly with laboratory use, have an offensive odor, and may induce immunologic hypersensitivity. Further, such displays require a considerable amount of time to set out for laboratory display.

It has therefore become desirable to provide some means by which anatomical organs may be preserved for study purposes over indefinite periods of time without requiring special care and attention that has previously been required for wet laboratory specimens.

Most prior apparatus associated with this field has been utilized for the purpose of preparing sections for viewing through a microscope. Although the methods utilized for these processes are sound, they are intended for use with microscopic specimens rather than for larger display purposes.

For example, it is often desirable to study serialed sections of anatomical organs such as the brains of larger animals. Serialed displays of accurately and equally cut sections of specimens allow an in-depth understanding of the anatomical structure of the organ at various planes through its thickness.

United States Pat. No. 2,996,762, granted to McCormick in 1961, discloses an imbedding structure and method for imbedding of specimens, tissues, cell structures and the like for use in biological studies. This method makes use of paraffin wax for imbedding a specimen. A molding process enables the imbedded specimen to be sliced by a microtome for slide viewing on a microscope. No process is disclosed for preparing the sliced specimens and surrounding wax in a permanent display nor is there any permanent display fixture for displaying serialed sections shown nor taught by this patent.

United States Pat. No. 2,776,596 granted to Eigen in 1957, discloses the preparation and mounting of specimen sections. In this patent, a specimen is suspended within a matrix solution which hardens about the specimen to form a semi-rigid block. This block includes alignment holes for receiving alignment pins of a slicing machine and similar alignment pins of a microscope slide mount. The holes and pins provide for accurate location of the imbedded specimen or slices of the specimen taken therefrom. It is intended that the specimen be sliced by a microtome with individual slices mounted to microscope slides for viewing purposes. No process or display device is shown for preserving the sliced specimens in a permanent display device.

It is a first object to provide a process and device by which serialed sliced macroscopic anatomical specimens can be preserved for long term display.

Another object is to provide such a process and device that will present an accurate representation of the sliced sections in a serialed array so that the viewer may develop a full understanding of the specimen on a plane basis.

A still further object is to provide such a process and device by which specimens may be displayed without requiring a considerable amount of time for laboratory setup.

A still further object is to provide such a display that is hermetically sealed and will thereby not produce an offensive odor as do wet stored specimens.

These and still further objects and advantages will become apparent upon reading the following detailed description of a preferred embodiment which, taken with the accompanying drawings, describe a preferred form of my invention. It is understood however that the following description is given by way of example to disclose a single preferred form of my invention. It is understood that other forms may be envisioned that are not touched by this description. It is therefore intended that only the following claims be taken as restrictions upon the scope and as definitions of my invention.

BRIEF DESCRIPTION OF THE DRAWINGS

A preferred form of the present invention is illustrated in the accompanying drawings in which:

FIG. 1 is a pictorial view of a specimen mounted within a block of transparent agar;

FIG. 2 is a schematic pictorial view of a rectangular array formed by sections of the agar block shown in FIG. 1;

FIG. 3 is a view illustrating the step of trimming the rectangular array;

FIG. 4 is a exploded pictorial view of the container and method by which it is assembled;

FIG. 5 is another pictorial view showing the assembled container and placement of a cover plate thereon;

FIG. 6 is a fragmentary view illustrating the procedure for fastening the cover plate to the container;

FIG. 7 is a pictorial view of the completed display; and

FIG. 8 is a fragmentary enlarged view of a corner of the container;

FIG. 9 is an enlarged section view taken substantially along line 9—9 in FIG. 8.

A DETAILED DESCRIPTION OF A PREFERRED EMBODIMENT

A specimen display is illustrated in FIGS. 7 through 9. The display is utilized to preserve and present for visual examination, serialed sections of a biological specimen 10 (FIG. 1). The display is shown being prepared in FIGS. 1 through 5. The finished display is shown in particular detail by FIGS. 7 through 9.

Although the present invention may be used with any anatomical organ specimen, this description will utilize a specific example — the brain of a dog. As shown in the drawings, the brain is prepared by slicing it into serialed sections. These sections 12 are then arranged relative to one another in a rectangular array 13 to be preserved within the present display device 16.

Before the display may be constructed, the specimen must be prepared. This is done firstly by suspending a specimen within a rectangular mold (not shown). The brain is suspended within the mold at least two centimeters from the bottom.

Once the brain has been properly positioned within the mold, a liquid transparent solidifying medium and preferably an agar-formalin solution is poured into the mold container to a level approximately three or four centimeters over the top surface of the brain. The solution is then allowed to cool and jell. Once the agar solution has jelled to a somewhat solidified consistency, the mold is removed, leaving a rectangular block as shown in FIG. 1 with the brain suspended at the approximate center.

Gross brain sections are prepared by slicing progressive sections of the agar-brain block through use of a guillotine type slicing machine (not shown). This is accomplished by first fixing the block to a guillotine mounting board with a hot, twenty percent gelatin solution. After the solution is applied between the agar-brain block and the mounting board, successive sections may be cut through the agar and brain with each section being cut along a parallel plane. Accurate forward indexing of the agar-brain block may assure that each section is equal in thickness.

The sliced agar-brain block is then re-assembled in a substantially rectangular array 13 as shown by FIG. 2. The sections are arranged in a specific order so the first cut section 12 is located in the upper left hand corner of the array. Succeeding sections are placed to the right of the first cut section. The next successive row starts immediately below the first cut section and proceeds from left to right. This process is continued until all sections have been laid out in a rectangular array and in an orderly sequence. The left to right sequence described above is convenient in that the sections may be "read" from left to right as are printed sentences.

If it is desired to arrange the array in a wide format and too few sections are present to complete the rectangular array, additional plain agar sections may be added to complete the rectangular configuration. These sections may be placed at the beginning or end of the serialed brain sections in order to complete the rectangular pattern.

The next step in formation of the display is to trim the sections 12 to be rid of excess agar solution and to present a more uniform rectangular array. This step is shown in FIG. 3. A scalpel 14 and a straight edge 15 may be used to trim the aligned rows or individual sections in order to produce straight horizontal rows and to eliminate excessive amounts of agar. When the array is complete, the finished serialed sections are arranged in a rectangular pattern that, as described, can be read like a page from left to right and from top to bottom.

Measurements are then taken of the total length and width of the rectangular array. Two sheets of transparent Plexiglas are then cut to these measurements. The two resulting Plexiglas sheets are utilized as a base plate 17 and a cover plate 18 of the present display device. It is preferrable that these two plates be cut simultaneously to assure that their dimensions are precisely identical.

The next step is to cut four strips of the same material to form upright sidewalls 19 of the display. The sidewalls may be divided into longitudinal walls 20 and transverse walls 21. The longitudinal walls 20 are cut to equal lengths and the transverse walls 21 are cut to lengths equal to the width of plates 17 and 18 plus the thickness of the two longitudinal walls 20. The transverse walls 21 will therefore transversely overlap the plates 17 and 18 to abut ends of longitudinal walls 20 as shown by FIGS. 6 and 8.

Once the plates 17 and 18 and sidewalls 19 are complete, the base plate 17 may be affixed to sidewalls 19. This is done by cementing peripheral edges 23 of base plate 17 to inside surfaces of sidewalls 19. Planar surfaces 24 and 25 of base plate 17 are located between rims 26 of walls 19 as shown in FIG. 9. The rims 26 thereby affords protection to the otherwise easily damaged surface 25 of base plate 17.

After securing base plate to sidewalls 19, a bead of silicone sealer 27 may be applied to the juncture between base plate 17 and sidewalls 19. The bead of sealer 27 is located on the outer side of base plate 17 so as not to interfere with reception of the rectangular specimen array along the remaining side 24.

Sidewalls 19 and base plate 17 form an upwardly open container into which the rectangular array 13 of sections 12 is received. Prior to this step, however, the container is flooded with a ten percent formal-saline preservation solution.

The brain sections are carefully laid out in this solution to eliminate all air bubbles between the sections and plate surface 24. Once the complete rectangular array has been transferred into the preservative flooded container, the remaining Plexiglas cover plate 18 is gently laid into position on top of the sections. A gentle downward pressure will force all air bubbles and excess preservative solution out between the edges of plate 18 and sidewalls 19. After completing this step, the cover plate 18 is completely immersed in the formal-saline preservative solution.

While the cover plate 18 is held in the immersed condition, a fastening means 28 is utilized to secure the cover plate 18 to the remainder of the container. Fastening means 28 is illustrated both in FIG. 6 and FIG. 8. As shown, fastening means 28 is simply comprised of a number of screws 29 that are threadably inserted through bore holes 30 formed in sidewalls 19. These screws engage peripheral edges 31 of cover plate 18. Fastening means 28 is utilized only to temporarily hold the cover plate in position while in its immersed condition and while the joint between plate 18 and walls 19 is sealed to hermetically seal the display. Placement of the screws 29 while the cover plate 18 is immersed serves to prevent re-entrainment of air between plates 17 and 18.

An exterior of surface 32 plate 18 is dried once the screws 29 are located. The junction of edges 31 and sidewalls 19 is continually wiped until the level of preservative solution is relocated just below the outside surface 32 of plate 18. The next step is then to cement the plate 18 to sidewalls 19. This is accomplished by applying an adhesive mixture of chloroform and plexiglass shavings to the exposed perimeter joints. This may be accomplished by utilizing a syringe and hypodermic needle.

After the adhesive hardens, the entire inside perimeter joint may be cleaned with an alcohol solution. Finally, another bead of silicone rubber 27 is applied about the perimeter. Beads 27 act as means to assure a hermetically sealed condition between the adjacent plates and surrounding walls 19. The sealing material will dry but will not completely harden, remaining flexible to complement the natural flexibility of the Plexiglas material utilized to produce the display.

The finished display 16 provides a visual representation of serialed, precisely cut sections of the brain. A viewer may develop a full understanding of the brain structure by comparing the various sections in sequence.

In the finished display 16, peripheral rims 26 of sidewalls 19 project outward of outer surfaces 25 and 32 of base plate 17 and cover plate 18 respectively. This dimension is preselected to be greater than the combined thicknesses of plates 17, 18 and the thickness of the equally sliced sections 12. Therefore, the rims 26, by projecting outward of the surfaces 25 and 32, will protect the plates 17 and 18 against damage when in use or in storage. The width of walls 19 also allows for varying thicknesses of specimen sections 12 in different individual displays while the overall thickness of the displays (between rims 26) remains equal. It is again noted that the above description is given only to present a preferred form of the present invention and that various changes and modifications may be made therein without departing from its intended scope. Therefore, only the following claims are to be taken as definitions of my invention.

What I claim is:

1. A process for preparing and mounting macroscopic sliced anatomical organ specimens comprising the steps of:
    a. suspending an anatomical organ within transparent solidifying medium such as agar solution;
    b. slicing the suspended organ and surrounding medium into sections of equal thicknesses;
    c. pouring a liquid preservative into an upwardly open transparent container;
    d. arranging the sliced sections in a prescribed array in the liquid preservative;
    e. pressing a transparent cover plate over the sections in the container to remove all air from between the cover plate and container; and
    f. affixing the transparent cover plate to the container to hermetically seal the sections and liquid preservative within the container under the transparent plate.

2. The process as recited by claim 1 wherein the step of arranging the sections in a prescribed array is accomplished by placing sections one next to another in a sequence denoting the order in which they were progressively sliced from the whole organ.

3. The process as recited by claim 2 wherein the sections are arranged in a rectangular array and wherein the arranging step further includes the step of trimming the sections in order to form straight horizontal rows with the rectangular array.

4. The process as recited by claim 1 wherein the transparent container is constructed according to the dimensions of the prescribed array by performing the steps of:
    producing a transparent base plate of dimensions equal to the prescribed array; and
    affixing wall members about the periphery of the base plate so that upper edges thereof project from one surface of the base plate a distance greater than the combined thicknesses of the base plate and organ sections.

5. The process as recited by claim 4 wherein the transparent cover plate is equal in dimension to the base plate.

6. The process as recited by claim 4 wherein the liquid preservative is poured to a sufficient level within the container to completely immerse the sections held therein.

7. The process as recited by claim 1 wherein the step of pressing the cover plate over the sections to remove entrained air is accomplished by pressing the cover plate into the container so that the cover plate becomes immersed in the preservative.

8. The process as recited by claim 7 wherein the step of affixing the cover plate is accomplished while the cover plate is immersed in the preservative liquid.

9. The process as recited by claim 8 wherein the container is constructed according to the dimensions of the prescribed array by performing the steps of:
    producing a transparent base plate of dimensions equal to the prescribed array; and
    affixing wall members about the periphery of the base plate so the upper edges thereof project from one surface of the base plate a distance greater than the combined thicknesses of the base plate and organ sections.

10. The process as recited by claim 9 wherein the cover plate is affixed to the container by:
    inserting screw fasteners through the wall members and into the cover plate while the plate is immersed in the preservative liquid;
    draining off the excess preservative; and
    applying a sealing compound about the joints formed between the cover plate and wall members.

11. A device for preserving and providing visual display of a uniformly sectioned anatomical organ, comprising:
    a transparent base plate having a planar surface;
    sidewalls on the base plate periphery having inside surfaces perpendicular to the planar surface and extending therefrom to peripheral rims;
    a transparent cover plate adapted to fit between the inside surfaces with a planar surface thereon spaced apart from the planar surface of the base plate by a distance corresponding to the thickness of an organ section held therebetween;
    means for fastening the cover plate to the side walls to maintain the spaced relation between the planar surfaces; and
    means for hermetically sealing the space between the planar plate surfaces.

12. The device as set out by claim 11 wherein the means for hermetically sealing the space between the planar plate surfaces is comprised of a flexible sealing material applied to the joint formed between the widewalls and cover plate.

13. The device as set out by claim 11 wherein the side walls, base plate and cover plate are separate elements adapted to be cut to a selected size corresponding to the size and number of organ sections to be displayed and wherein the side walls are joined to the base plate with adhesive.

14. The device as set out by claim 11 wherein the means for fastening the cover plate to the sidewalls is comprised of screw fasteners inserted through the sidewalls to engage the cover plate.

15. The device as set out by claim 14 wherein the means for fastening the cover plate to the sidewalls also includes an adhesive applied to adjacent portions of the cover plate and sidewalls.

* * * * *